United States Patent [19]
Quash

[11] Patent Number: 6,028,114
[45] Date of Patent: Feb. 22, 2000

[54] USE OF AMINOTHIOLESTER DERIVATIVES IN PHARMACEUTICS

[75] Inventor: Gerard Quash, Francheville, France

[73] Assignee: Galderma Research & Development, S.N.C., Valbonne, France

[21] Appl. No.: 09/202,068

[22] PCT Filed: Apr. 8, 1998

[86] PCT No.: PCT/FR98/00712

§ 371 Date: May 25, 1999

§ 102(e) Date: May 25, 1999

[87] PCT Pub. No.: WO98/44919

PCT Pub. Date: Oct. 15, 1998

[30] Foreign Application Priority Data

Apr. 8, 1997 [FR] France .................................. 97 04283

[51] Int. Cl.[7] ..................................................... A61K 31/13
[52] U.S. Cl. ........................... 514/665; 514/642; 514/666; 514/671; 514/676; 514/702; 514/704
[58] Field of Search ..................... 514/702, 642, 514/665, 666, 671, 676, 704

[56] References Cited

U.S. PATENT DOCUMENTS 5,744,499  4/1998  Quash et al. ............................ 514/639

FOREIGN PATENT DOCUMENTS 0 133 407  2/1985  European Pat. Off. .
96 20701   7/1996  WIPO .

*Primary Examiner*—Frederick Krass
*Attorney, Agent, or Firm*—Burns, Doane, Swecker & Mathis, L.L.P.

[57] ABSTRACT

Use of at least one aminothiol ester derivative for the preparation of a pharmaceutical composition intended to increase the inhibition of a character resistant to the induction of apoptosis of transformed cells, this character being due to the bc12 gene present in these cells. The pharmaceutical composition is more particularly intended to treat pathologies chosen from breast cancers, B cell lymphomas, leukaemias, neuroblastomas, adenocarcinomas of the prostate, prolactinomas and other pituitary adenomas.

19 Claims, 3 Drawing Sheets

USE OF AMINOTHIOLESTER DERIVATIVES IN PHARMACEUTICS

This application is a 371 of PCT/FR98/00712, filed Apr. 08, 1998.

The present invention relates to the use of aminothiol ester derivatives in the preparation of a pharmaceutical composition for increasing the inhibition of apoptosis due to the presence of the $bcl_2$ gene in transformed cells.

There are two types of mechanism involved in cell death. The first, of a conventional type, is called necrosis. Morphologically, necrosis is characterized by swelling of the mitochondria and of the cytoplasma and by nuclear impairment, followed by the destruction of the cell and its autolysis, this being accompanied by an inflammation phenomenon. Necrosis occurs in a passive and incidental manner. Tissue necrosis is generally due to a physical trauma of cells or a chemical poison, for example.

The other form of cell death is called apoptosis [Kerr, J. F. R. and Wyllie, A. H., Br. J. Cancer, 265, 239 (1972)]; however, unlike necrosis, apoptosis does not cause an inflammation phenomenon. It has been described that apoptosis can occur under different physiological conditions. It is a highly selective form of cellular suicide which is characterized by easily observable morphological and biochemical phenomena. Thus, condensation of chromatin associated or otherwise with an endonuclease activity, the formation of apoptotic bodies and fragmentation of deoxyribonucleic acid (DNA) by the activation of endonucleases into DNA fragments of 180–200 base pairs (these fragments can be observed by agarose gel electrophoresis), have been observed in particular.

Apoptosis may be considered as a programmed cell death involved in tissue development, differentiation and renewal. It is also considered that the differentiation, growth and maturation of cells are closely linked to apoptosis and that substances capable of playing a role in the differentiation, growth and maturation of cells are also linked to the phenomenon of apoptosis.

There has already been described in patent application WO 96-20701 filed by the applicant a compound chosen from methional, malondialdehyde and any factor increasing the intracellular level of methional or of malondialdehyde for use as medicament, this medicament being more particularly intended to increase the phenomenon of programmed cell death (apoptosis) and thus making it possible to treat numerous diseases, more particularly diseases linked to cell hyperproliferation, such as in the case of cancer, autoimmune diseases or allergies. However, the addition of exogenous methional to cells in culture inhibits the growth of transformed cells just as much as that of normal cells.

In order to try to increase the level of endogenous methional in transformed cells, but not in normal cells, its metabolism was studied.

Thus, in the metabolism of methional, it is known that 4-methylthio-2-oxobutanoic acid can be metabolized in vivo by the branched chain oxoacid-dehydrogenase complex present in the mitochondria of cells of the liver, heart and skeletal muscle via methional to give methylthiopropionyl-CoA [cf. Wu, G. & Yeaman, S. J. (1989) Biochem. J. 257, 281–284; Haussinger, D., Stehle, T. & Gerok, W. (1985) J. Biol. Chem. 366, 527–536; Jones, S. M. A. & Yeaman, S. J. (1986) Biochem. J. 237, 621–623]. It has also been described that methylthio-2-oxobutanoic acid can be metabolized in vivo by transamination into methionine [cf. Ogier, G., Chantepie, J., Deshayes, C., Chantegrel, B., Charlot, C., Doutheau, A. & Quash, G. (1993) Biochem. Pharmacol. 45, 1631–1644]. Methional can also possibly be reduced or oxidized respectively into methionol by an aldehyde reductase or into methylthiopropionic acid by an aldehyde dehydrogenase. Finally, methional, in combination with the HO* radical, can give malondialdehyde and methane thiol by a β-hydroxylation reaction [Quash, G., Roch, A. M., Chantepie, J., Michal, Y., Fournet, G., and Dumontet, C. (1995) Biochem. J. 305, 1017–1025].

In the text which follows, the following abbreviations may be used:

MTOB represents 4-methylthio-2-oxobutanoic acid;
MTPA represents methylthiopropionic acid;
E1 represents the decarboxylase of the branched chain oxoacid-dehydrogenase complex whose cofactor is thiamine pyrophosphate (TPP);
E2 represents the transacylase of the branched chain oxoacid-dehydrogenase complex whose cofactor is thioctic acid (TA);
ALDR represents aldehyde reductase;
ALDH represents aldehyde dehydrogenase.

It has also been described that inhibitors of the transaminase which is involved in the conversion of MTOB to methionine, which are compounds of esters of L-methionine and pyridoxal, selectively inhibit the growth of several types of transformed cells but not that of normal cells MRC5 and weakly induce apoptosis also in the lymphoid cells BAF3 cultured in the presence of interleukin-3.

In the case of pathologies which are characterized by an overexpression of the bc12 gene, such as in particular breast cancers, B cell lymphomas, leukaemias, neuroblastomas, adenocarcinomas of the prostate, prolactinomas and other pituitary adenomas, this overexpression of the bc12 gene confers on the cells resistance to apoptosis and therefore to chemotherapy and to antiandrogens (Miyashita, T. and Reed, J. C. (1993) Blood 81, 151–157; Furuya, Y. et al. (1996) Clinical Cancer Research 2, 389–398).

Moreover, it has been described that the addition of an inhibitor of the enzyme ALDH, disulfiram (at 50 µm), to BAF3- bo cells induced fragmentation in 30% of cellular DNA, typical of apoptosis, whereas in BAF3-bc12 cells which are resistant to apoptosis, this increase did not exceed 5% (Roch, A.-M. et al., (1996) Biochem. J. 313, 973–981). The increase in the concentration of disulfiram did not make it possible to obtain a higher percentage of fragmentation because of the intrinsic toxicity of this product.

One of the aims of the present invention is therefore to partially, or even completely, inhibit this character resistant to induction of apoptosis due to the bc12 gene present in transformed cells.

This aim and others are achieved by the is present invention which relates to the use of at least one aminothiol ester derivative of formula (I) for the preparation of a pharmaceutical composition intended to lift the inhibition of a character resistant to the induction of apoptosis of transformed cells, this character being due to the bc12 gene present in these cells.

The present invention also relates to the use of at least one aminothiol ester derivative of formula (I) for the preparation of a pharmaceutical composition intended to increase the inhibition of the character resistant to chemotherapy or to antiandrogens of transformed cells.

More particularly, the character resistant to chemotherapy or to antiandrogens of transformed cells is due to the bc12 gene present in these cells.

The aminothiol ester derivatives have the following formula (I):

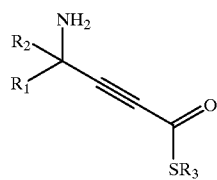

in which $R_1$, $R_2$ and $R_3$, independently, represent a saturated or unsaturated, linear or branched $C_1$–$C_6$ alkyl radical.

Among the saturated linear alkyl radicals having from 1 to 6 carbon atoms, there may be mentioned in particular the methyl, ethyl, propyl, butyl, pentyl and hexyl radicals.

Among the saturated branched alkyl radicals having from 1 to 6 carbon atoms, there may be mentioned in particular the 2-methylbutyl, 2-methylpentyl, isopropyl and tert-butyl radicals.

Among the unsaturated alkyl radicals having from 1 to 6 carbon atoms, there may be mentioned in particular the allyl radical.

Preferably, $R_1$, $R_2$ and $R_3$ independently represent a $C_1$ to $C_3$ alkyl radical.

Preferably, $R_1$ and $R_2$ represent a methyl radical and $R_3$ a radical chosen from the methyl, ethyl and propyl radical.

Advantageously, $R_1$, $R_2$ and $R_3$ represent the methyl radical.

There is advantageously used a compound of formula (I) in which the amine is in the ammonium form, preferably in the organic ammonium form and advantageously in the ammonium formate or acetate form. In the ammonium form, the compounds of formula (I) have the advantage of being water-soluble, and can therefore be easily used.

These compounds can be obtained by (1) reacting a dialkylpropargylamine derivative, in which the amine functional group is protected (these compounds are described in patent application EP 0,133,407), with a very strong base in order to give the carbanion of the propargyl radical, (2) this carbanion is then reacted with a carbon oxysulphide, and then (3) an alkylation reaction is carried out on the sulphur of the product obtained in (2), and finally (4) the amine is deprotected. Any means known per se is used in order to obtain the compound of formula (I) in the ammonium form. Thus, in order to obtain the compound of formula (I) in the ammonium formate or acetate form, the compound obtained in step (4) is reacted with formic acid or acetic acid, respectively.

Other characteristics, aspects, objects and advantages of the invention will emerge even more clearly on reading the description which follows, as well as the various concrete, but not at all limiting, examples intended to illustrate it.

Figure 1:
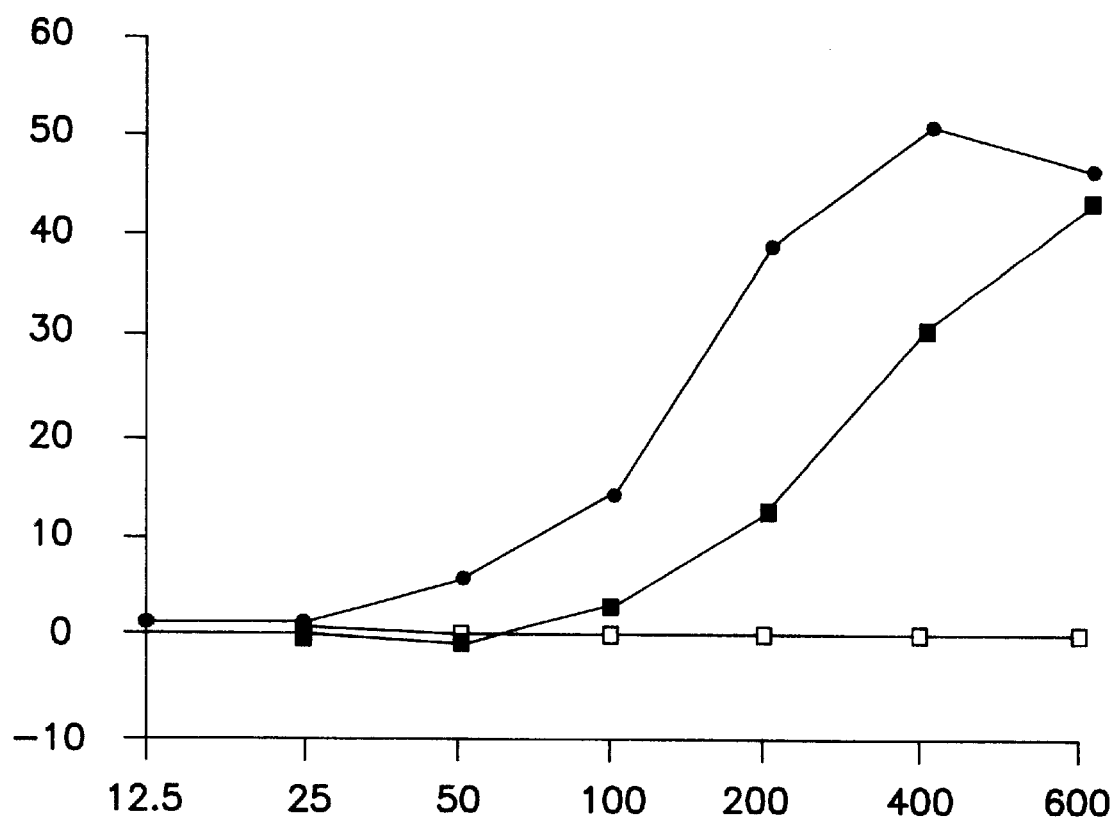
FIG. 1 represents the percentage of DNA fragments obtained in BAF-bc12 wells cultured for 6 hours with different compounds as a function of the concentrations (expressed in $\mu$M) of these different compounds which are: 4-amino-4-methyl-2-pentyn-1-al (represented by □), S-methyl 4-amino-4-methylpent-2-ynethioate (represented by ■) and the mixture of S-methyl 4-amino-4-methylpent-2-ynethioate (at different concentrations) and of methional at 200 $\mu$M (represented by ●).

These compounds of formula (I) which inhibit the activity of the enzyme ALDH have the advantage of being of the "suicide" type (irreversible covalent bonding with the enzyme ALDH), of not being toxic and of inhibiting the growth of transformed (cancerous) cells and not that of normal cells.

The pathologies which are characterized by an overexpression of the bc12 gene are in particular breast cancers, B cell lymphomas, leukaemias, neuroblastomas, adenocarcinomas of the prostate, prolactinomas and other pituitary adenomas.

The pharmaceutical composition according to the invention comprises a physiologically acceptable medium.

The administration of the composition according to the invention may be carried out by the enteral, parenteral, topical or ocular route. Preferably, the pharmaceutical composition is packaged in a form suitable for application by the systemic route (for injection or infusion).

By the enteral route, the composition, more particularly the pharmaceutical composition, may be provided in the form of tablets, gelatine capsules, sugar-coated tablets, syrups, suspensions, solutions, powders, granules, emulsions, lipid or polymeric microspheres or nanospheres or vesicles allowing a controlled release. By the parenteral route, the composition may be provided in the form of solutions or suspensions for infusion or for injection.

The compounds of formula (I) according to the invention are generally administered at a daily dose of about 0.001 mg/kg to 100 mg/kg of body weight in 1 to 3 doses.

By the topical route, the pharmaceutical composition according to the invention is more particularly intended for the treatment of the skin and of the mucous membranes and may be provided in the form of salves, creams, milks, ointments, powders, impregnated pads, solutions, gels, sprays, lotions or suspensions. It may also be provided in the form of lipid or polymeric microspheres or nanospheres or vesicles or of polymeric patches and hydrogels allowing controlled release. This composition for topical administration may be provided either in anhydrous form, or in aqueous form.

By the ocular route, the composition comprises mainly collyria.

The compounds of formula (I) are used by the topical or ocular route at a concentration which is generally of between 0.0001% and 10% by weight, preferably between 0.01 and 1% by weight, relative to the total weight of the composition.

The compositions as described above may of course contain in addition inert or even pharmacodynamically active additives or combinations of these additives, and in particular: methional, numerous antineoplastic agents, such as for example dexamethasone, cyclophosphamide, cisplatin, etoposide and BCNU (N,N-bis(2-chloroethyl)-N-nitrosourea), which are also capable of inducing apoptosis.

Thus, the subject of the present invention is also a pharmaceutical composition characterized in that it comprises, in a physiologically acceptable carrier, at least one compound of formula (I), as described above, and at least one compound chosen from methional and an antineoplastic agent.

This composition is therefore more particularly intended to treat, preventively or curatively, diseases linked to cell hyperproliferation, such as cancers, autoimmune diseases or allergies.

The pharmaceutical composition preferably comprises methional and at least one compound of formula (I), as described above.

Preferably, the antineoplastic agent is capable of inducing apoptosis and may thus be chosen from those cited above.

The composition according to the invention may be in the form of a kit comprising at least one compound of formula (I), as described above, and at least one compound chosen from methional and an antineoplastic agent, the compounds in this kit being packaged separately.

Of course, persons skilled in the art will be careful to choose the possible compound(s) to be added to these compositions such that the advantageous properties intrinsically attached to the present invention are not, or not substantially, adversely affected by the addition envisaged.

Several examples intended to illustrate the present invention will now be given with no limitation being implied.

EXAMPLE 1

Process for the preparation of S-methyl 4-amino-4-methylpent-2-ynethioate 16 ml of a 1.5 M solution of n-butyllithium in hexane are added, over 5 minutes at $-70°$ C., to a solution of 4.51 g (20 mM) of N,N-(1,2-bis(dimethylsilyl)ethane)-1,1-dimethylpropargylamine (described in patent application EP 0,133,407) in 100 ml of tetrahydrofuran. The reaction medium is allowed to return to room temperature over 30 minutes and then stirred for a further 1 hour at this temperature (18° C.). After returning to $-70°$ C., there are added by means of a cannula-like tube 9 ml of carbon oxysulphide previously condensed. After stirring for one hour at $-70°$ C. and then for 30 minutes at $+3°$ C., 1.31 ml (21 mM) of methyl iodide are added and the stirring is continued for 2 hours at this temperature. After dilution in 400 ml of ether, the mixture is washed with a saturated sodium chloride solution, dried over sodium sulphate and evaporated to dryness; the amine is unblocked on a silica gel as described in patent application EP 0,133,407, and 2 g (63%) of amine are thus isolated.

EXAMPLE 2

Process for the preparation of S-methyl 4-amino-4-methylpent-2-ynethioate 2.7 mM formic acid dissolved in 2 ml of ether at 0° C. are added to 418 mg (2.7 mM) of the amine obtained in Example 1 in anhydrous ether. The mixture is stirred for 5 minutes and then brought to room temperature and evaporated to dryness. After taking up in anhydrous ether, the solid is dispersed and the supernatant removed, and then the product is dried under vacuum and 415 mg (77%) of the desired amine formate are isolated.

EXAMPLE 3

Effect of different compounds on the induction of apoptosis in BAF3-b0 and BAF3-bc12 cells The cells used correspond to a mouse lymphocytic cell line BAF3 which requires interleukin-3 (IL3) to grow and which undergoes apoptosis (more than 80% of the cells) in the absence of IL3 within 16 hours [cf. Collins, M. K. L., Marvel, J., Malde, P. & Lopez-Rivas, A. (1992) J. Exp. Med. 176, 1043–1051].

The BAF3-bc12 cells correspond to BAF3 cells transfected with the bc12 gene, the BAF3-b0 cells correspond to BAF3 cells not transfected with the bc12 gene. As specified above, the BAF3-b0 cells undergo apoptosis (more than 80% of the cells) in the absence of IL3 within 16 hours. On the other hand, the BAF3-bc12 cells, which are therefore transfected with the bc12 gene, show no sign of apoptosis in the absence of IL3.

The BAF3-b0 or BAF3-bc12 cells, cultured in the presence of IL3, are labelled by an adaptation of the method described in Wright, S. et al. (1992) J. of Cell. Biochem. 48, 344–355, by incubating $2.5 \times 10^5$ cells/ml with 0.5 µCi [3H] thymidine for 40 hours at 37° C. After two washes with a culture medium, $2.5 \times 10^6$ cells are cultured in the presence of different compounds to be tested. After incubating for 6 hours, these cells are recovered by centrifugation at 400 g for 5 minutes and washed 3 times in PBS buffer. The cells recovered in the pellet are lysed in 2 ml of 0.1% Triton X-100, 20 mM EDTA, 5 mM Tris pH 8 and centrifuged at 30,000 g at 4° C. for 30 minutes. The supernatants are recovered and the pellets dissolved in 0.3 ml of 0.5 N NaOH. Aliquots of the culture medium (1 ml), of the supernatant (0.3 ml) and of the solubilized pellet (0.1 ml) are assayed in a scintillation counter. The percentage of DNA fragments is calculated in the following manner:

$$\text{\% of DNA fragments} = \frac{\text{dpm for the culture medium} + \text{dpm for the supernatant}}{\text{dpm for the culture medium} + \text{dpm for the supernatant} + \text{dpm for the solubilized pellet}}$$

Figure 2:
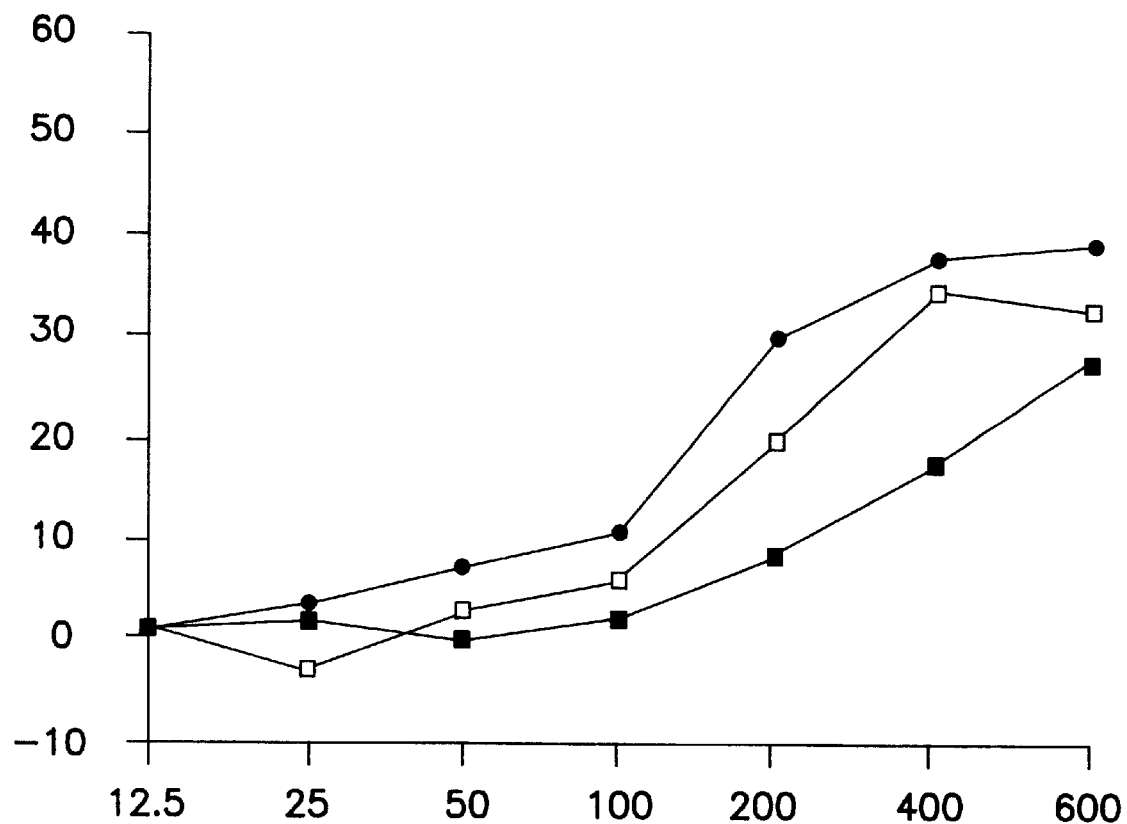
FIG. 2 represents the percentage of DNA fragments obtained in BAF-b0 cells cultured for 6 hours with different compounds as a function of the concentrations (expressed in $\mu$M) of these different compounds which are: 4-amino-4-methyl-2-pentyn-1-al (represented by □), S-methyl 4-amino-4-methylpent-2-ynethioate (represented by ■) and the mixture of S-methyl 4-amino-4-methylpent-2-ynethioate (at different concentrations) and of methional at 200 $\mu$M (represented by ●).

The results are assembled in FIGS. 1 and 2.

The results for 4-amino-4-methyl-2-pentyn-2-al are given by way of comparison. 4-Amino-4-methyl-2-pentyn-1-al (represented by □) is also an inhibitor of ALDH but does not correspond to the compound of formula (I) used in the present invention. The process for its production is described in patent application EP 0,133,407.

S-Methyl 4-amino-4-methylpent-2-ynthioate is the compound obtained according to the process described in Example 1.

These results clearly show that the presence of S-methyl 4-amino-4-methylpent-2-ynthioate, preferably in combination with methional, makes it possible to lift the inhibition of apoptosis due to the bc12 gene in BAF3-bc12 cells. The methional-S-methyl 4-amino-4-methylpent-2-ynthioate combination is particularly advantageous because it offers synergy in the lifting of the inhibition of apoptosis; indeed, alone at 200 µm, methional exhibits no activity (0% of DNA fragments).

EXAMPLE 4

Effect of S-methyl 4-amino-4-methylpent-2-ynthioate on the induction of apoptosis in LNCaP cells The cells used correspond to a prostate adenocarcinoma cell line LNCaP (ATCC CRL 1740). The LNCaP cells are cultured in a medium containing RPMI 1640 medium (marketed by the company GIBCO) and 7.5% foetal calf serum. They are labelled by an adaptation of the method described in Wright, S. et al. (1992) J. of Cell. Biochem. 48, 344–355, by incubating $2.5 \times 10^5$ cells/ml with 0.5 µCi [3H] thymidine for 5 days at 37° C. After two washes with PBS buffer, $2.5 \times 10^6$ cells are reincubated in a fresh culture medium containing RPMI 1640 medium, 7.5% foetal calf serum and S-methyl 4-amino-4-methylpent-2-ynthioate at appropriate doses. After incubating for 6 hours, these cells are recovered by centrifugation at 400 g for 5 minutes and washed 3 times in PBS buffer. The cells recovered in the pellet are lysed in 2 ml of 0.1% Triton X-100, 20 mM EDTA, 5 mM Tris pH 8 and centrifuged at 30,000 g at 4° C. for 30 minutes. The supernatants are recovered and the pellets dissolved in 0.3 ml of 0.5 N NaOH. Aliquots of the culture medium (1 ml), of the supernatant (0.3 ml) and of the solubilized pellet (0.1 ml) are assayed in a scintillation counter. The percentage of DNA fragments is calculated in the following manner:

$$\% \text{ of DNA fragments} = \frac{\text{dpm for the culture medium} + \text{dpm for the supernatant}}{\text{dpm for the culture medium} + \text{dpm for the supernatant} + \text{dpm for the solubilized pellet}}$$

Figure 3:
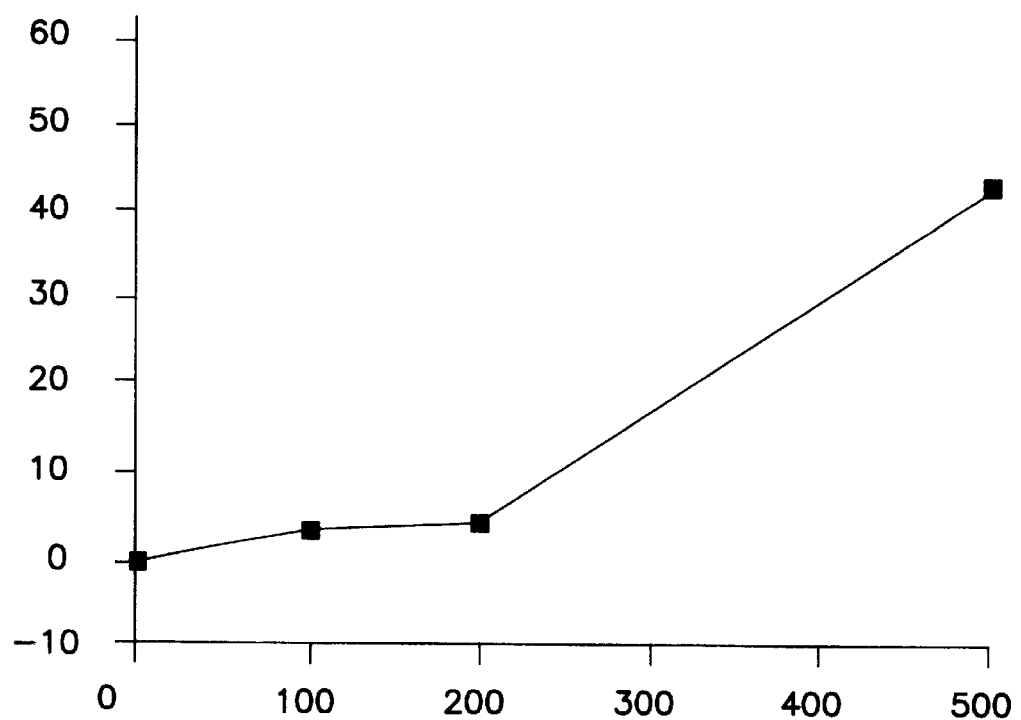
FIG. 3 represents the percentage of DNA fragments obtained in LNCaP cells (ATCC CRL 1740) cultured for 6 days with S-methyl 4-amino-4-methylpent-2-ynethioate (represented by ■) as a function of the concentrations of this compound (expressed in $\mu$M).

The results are assembled in FIG. 3.

These results show clearly that the presence of S-methyl 4-amino-4-methylpent-2-ynthioate makes it possible to lift the inhibition of apoptosis due to the bc12 gene in the LNCaP cells.

I claim:

1. A method for partially or completely inhibiting resistance to induction of apoptosis of transformed cells, said resistance existing due to the bc12 gene present in said cells, said method comprising administering an effective amount of at least one aminothiol ester derivative of the following formula (I):

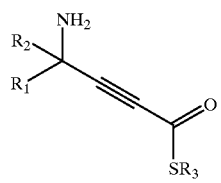

wherein $R_1$, $R_2$ and $R_3$, independently, represent a saturated or unsaturated, linear or branched $C_1$–$C_6$ alkyl radical, to a patient in need of and susceptible to such inhibition.

2. The method according to claim 1, wherein the aminothiol ester derivative has a formula (I) wherein $R_1$, $R_2$ and $R_3$, independently, represent radicals comprising methyl, ethyl, propyl, butyl, pentyl, hexyl, 2-methylbutyl, 2-methylpentyl, isopropyl, tert-butyl or allyl radicals.

3. The method according to claim 2, wherein $R_1$, $R_2$ and $R_3$ independently, represent a $C_1$ to $C_3$ alkyl radical.

4. The method according to claim 3, wherein $R_1$, $R_2$ and $R_3$ represent a methyl radical.

5. The method according to claim 1, wherein the compound of formula (I) has the amine radical in the ammonium form.

6. The method according to claim 5, wherein said compound is in the organic ammonium form.

7. The method according to claim 6, wherein said compound is in the formate or acetate form.

8. A method for partially or completely inhibiting resistance to chemotherapy or to antiandrogens of transformed cells, said method comprising administering an effective amount of at least one aminothiol ester derivative of the following formula (I):

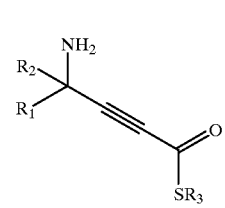

wherein $R_1$, $R_2$ and $R_3$, independently, represent a saturated or unsaturated, linear or branched $C_1$–$C_6$ alkyl radical to a patient in need of and susceptible to such inhibition.

9. The method according to claim 8, wherein the resistance to chemotherapy or to antiandrogens of transformed cells is due to the bc12 gene present in said cells.

10. The method according to claim 9, wherein the aminothiol ester derivative has a formula (I) wherein $R_1$, $R_2$ and $R_3$, independently, represent radicals comprising methyl, ethyl, propyl, butyl, pentyl, hexyl, 2-methylbutyl, 2-methylpentyl, isopropyl, tert-butyl or allyl radicals.

11. The method according to claim 10, wherein $R_1$, $R_2$ and $R_3$ independently, represent a $C_1$ to $C_3$ alkyl radical.

12. The method according to claim 11, wherein $R_1$, $R_2$ and $R_3$ represent a methyl radical.

13. The method according to claim 8, wherein the compound of formula (I) has the amine radical in the ammonium form.

14. The method according to claim 13, wherein said compound is in the organic ammonium form.

15. The method according to claim 14, wherein said compound is in the formate or acetate form.

16. A pharmaceutical composition comprising an effective amount of at least one aminothiol ester derivative of the following formula (I):

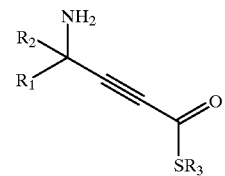

wherein $R_1$, $R_2$ and $R_3$, independently represent a saturated or unsaturated, linear or branched $C_1$–$C_6$ alkyl radical and methional and/or another antineoplastic agent.

17. The pharmaceutical composition according to claim 16, wherein methional is present along with the compound of formula (I).

18. A method for treating a patient suffering from or at increased risk for diseases causally linked to cellular hyperproliferation comprising administering an effective amount of at least one aminothiol ester derivative of the following formula (I):

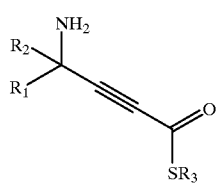

(I)

wherein $R_1$, $R_2$ and $R_3$, independently, represent a saturated or unsaturated, linear or branched $C_1$–$C_6$ alkyl radical, to a patient in need of susceptible to such treatment.

19. A method for treating a patient suffering from or at increased risk for diseases comprising breast cancers, B cell lymphomas, leukemias, neuroblastomas, adenocarcinomas of the prostate, prolactinomas or other pituitary adenomas, said method comprising administering an effective amount of at least one aminothiol ester derivative of the following formula (I):

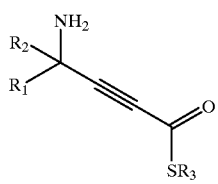

(I)

wherein $R_1$, $R_2$ and $R_3$, independently, represent a saturated or unsaturated, linear or branched $C_1$–$C_6$ alkyl radical to a patient in need of and susceptible to such treatment.

* * * * *